United States Patent
Vo et al.

(10) Patent No.: US 10,800,964 B2
(45) Date of Patent: *Oct. 13, 2020

(54) DUAL FUNCTIONING CORROSION INHIBITOR AND FOAMING AGENT

(71) Applicant: Multi-Chem Group LLC, Houston, TX (US)

(72) Inventors: Loan K. Vo, Houston, TX (US); Deepak S. Monteiro, Houston, TX (US); Philippe Prince, Pearland, TX (US); Shane Wyatt Rorex, New Caney, TX (US)

(73) Assignee: Multi-Chem Group, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,943

(22) Filed: Jul. 16, 2019

(65) Prior Publication Data

US 2020/0095493 A1 Mar. 26, 2020

Related U.S. Application Data

(60) Provisional application No. 62/734,070, filed on Sep. 20, 2018.

(51) Int. Cl.
*E21B 41/02* (2006.01)
*E21B 43/12* (2006.01)
(Continued)

(52) U.S. Cl.
CPC ............ *C09K 8/584* (2013.01); *C07C 233/36* (2013.01); *C07C 233/38* (2013.01);
(Continued)

(58) Field of Classification Search
None
See application file for complete search history.

(56) References Cited

U.S. PATENT DOCUMENTS

| 4,741,844 A | 5/1988 | Posey, Jr. |
| 4,796,702 A * | 1/1989 | Scherubel .............. C09K 8/536 |
| | | 166/308.6 |

(Continued)

FOREIGN PATENT DOCUMENTS

| CN | 101838527 | 3/2009 |
| CN | 105439885 | 2/2018 |
| WO | 2007044166 A2 | 4/2007 |

OTHER PUBLICATIONS

Pakulski, M., & Martin, R., Synergism and Antagonism of Foaming Agents and Corrosion Inhibitors, SPE International Symposium on Oilfield Chemistry, SPE65016, 2001.

(Continued)

*Primary Examiner* — Andrew Sue-Ako
(74) *Attorney, Agent, or Firm* — Tenley Krueger; C. Tumey Law Group PLLC

(57) ABSTRACT

A method may include: placing into a wellbore penetrating a subterranean formation a foaming agent, wherein the wellbore comprises a produced fluid from the subterranean formation; and foaming the produced fluid. The foaming agent may include at least one of the following structures:

(Continued)

-continued

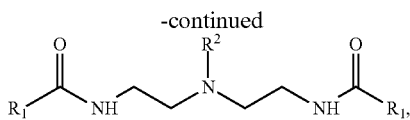

wherein R1 and R2 are individually selected from an alkyl group, an alkenyl group, a heteroatom substituted alkyl group, or a heteroatom substituted alkenyl group, wherein R1 comprises 5 carbon atoms to 22 carbon atoms in length, and wherein R2 comprises 1 carbon atom to 8 carbon atoms.

13 Claims, 5 Drawing Sheets

(51) Int. Cl.
| | |
|---|---|
| C09K 8/584 | (2006.01) |
| C09K 8/594 | (2006.01) |
| C09K 8/54 | (2006.01) |
| C07C 233/36 | (2006.01) |
| C07C 233/38 | (2006.01) |
| E21B 43/16 | (2006.01) |
| C07D 233/24 | (2006.01) |

(52) U.S. Cl.
CPC .............. *C07D 233/24* (2013.01); *C09K 8/54* (2013.01); *C09K 8/594* (2013.01); *E21B 41/02* (2013.01); *E21B 43/121* (2013.01); *E21B 43/16* (2013.01); *C09K 2208/32* (2013.01)

(56) References Cited

U.S. PATENT DOCUMENTS

| | | | |
|---|---|---|---|
| 8,551,925 B2 | 10/2013 | Nguyen et al. | |
| 2006/0076145 A1* | 4/2006 | Lembcke | E21B 41/0078 166/372 |
| 2011/0071060 A1* | 3/2011 | Nguyen | C09K 8/38 507/265 |
| 2012/0279715 A1 | 11/2012 | Nguyen et al. | |
| 2016/0272875 A1* | 9/2016 | Ghumare | C09K 8/86 |
| 2020/0087566 A1* | 3/2020 | Prince | C09K 8/52 |

OTHER PUBLICATIONS

McCormack, P. et al., "Liquid chromatography/electrospray ionisation mass spectrometric investigations of imidazoline corrosion inhibitors in crude oils", Rapid Commun. Mass Spectrom., 2002, vol. 16, pp. 705-712 See abstract; and p. 706, left column.

International Search Report and Written Opinion for PCT Application No. PCT/US2019/042087 dated Oct. 31, 2019.

* cited by examiner

DUAL FUNCTIONING CORROSION INHIBITOR AND FOAMING AGENT

BACKGROUND

During production of formation fluids such as oil and gas from a subterranean formation, a differential pressure from the producing zone of the subterranean formation to the surface may provide the driving force to produce the formation fluids. As a subterranean formation is drained, oil, water, and gas produced from the subterranean formation may flow into the wellbore penetrating the subterranean formation and be transported through the wellbore to a surface such as a wellhead. There may be a column of produced fluid present in the wellbore above a producing zone of the subterranean formation which may exert a hydrostatic pressure on the subterranean formation and serve to decrease the pressure differential between the subterranean formation and the surface. The decreased differential pressure may cause the production of formation fluids to slow down or cease.

Some efforts have been made to reduce the density of the column of formation fluid such as by foaming, for example. However, forming a stable hydrocarbon foam may be difficult as some hydrocarbons may exhibit anti-foaming properties thereby preventing foam formation or breaking down foam as it forms. Fluorosurfactants have been developed to foam hydrocarbon fluids but these types of surfactants are often costly and not environmentally friendly, requiring special handling and use instructions. Furthermore, fluorosurfactants may be corrosive to metals used in downhole applications, thereby leading to reduced lifetime of well components and potential of necessary remediation procedures.

BRIEF DESCRIPTION OF THE DRAWINGS

These drawings illustrate certain aspects of some of the present disclosure and should not be used to limit or define the disclosure.

DETAILED DESCRIPTION

Figure 1:
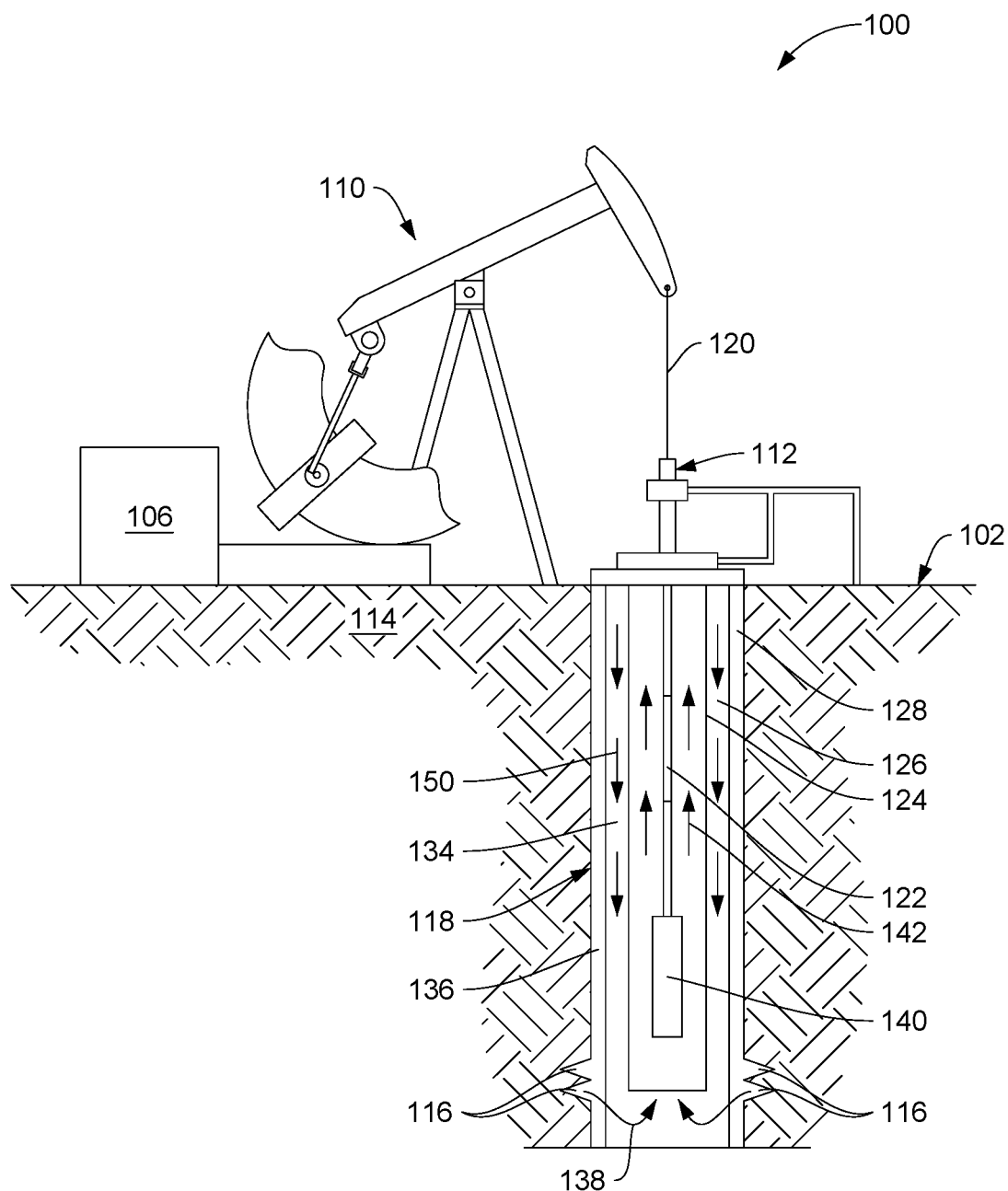
FIG. 1 is a schematic illustration of example secondary lift system including a treatment fluid.

A foaming agent that has foaming and corrosion inhibition properties is provided. The foaming agent may be introduced alone or as part of a treatment fluid into a producing wellbore. A treatment fluid may include a carrier fluid and the foaming agent. In an example, the foaming agent or a treatment fluid containing the foaming agent may be introduced into a wellbore and a produced fluid in the wellbore may be foamed. The foaming agent may provide surfactant properties thereby allowing hydrocarbons and/or hydrocarbons and water present the wellbore to be foamed. In another example, the foaming agent or a treatment fluid containing the foaming agent may be introduced into the wellbore alongside a foaming gas. Additionally, the foaming agent may provide some degree of corrosion resistance to tubulars and other downhole equipment. As used herein, the term "corrosion inhibitor" refers to be any compound capable of inhibiting or slowing the corrosion rate of a metal or a metal alloy. As used herein, the term "inhibit" and its derivatives refer to lessening the tendency of a phenomenon to occur and/or the degree to which that phenomenon occurs. The term "inhibit" does not imply any particular degree or amount of inhibition.

The foaming agent may include compositions with structure 1, for example.

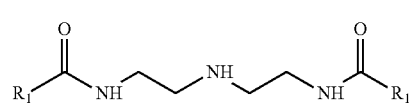

Structure 1

In Structure 1, R1 may be selected from an alkyl group, an alkenyl group, a heteroatom substituted alkyl group, or a heteroatom substituted alkenyl group. Suitable heteroatoms that may be substituted may include, but are not limited to, nitrogen, oxygen, and sulfur, among others. The alkyl or alkenyl (or heteroatom substituted) group R1 may include from 5 carbon atoms to 22 carbon atoms. Alternatively, R1 may include 5 carbon atoms to 6 carbon atoms, 6 carbon atoms to 8 carbon atoms, 8 carbon atoms to 12 carbon atoms, 12 carbon atoms to 16 carbon atoms, 16 carbon atoms to 20 carbon atoms, or 20 carbon atoms to 22 carbon atoms.

The foaming agent may further include compositions with Structure 2 for example.

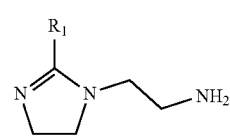

Structure 2

In Structure 2, R1 may be selected from an alkyl group, an alkenyl group, a heteroatom substituted alkyl group, or a heteroatom substituted alkenyl group. Suitable heteroatoms that may be substituted may include, but are not limited to, nitrogen, oxygen, and sulfur, among others. The alkyl or alkenyl (or heteroatom substituted) group R1 may include 5 carbon atoms to 22 carbon atoms. Alternatively, R1 may include 5 carbon atoms to 6 carbon atoms, 6 carbon atoms to 8 carbon atoms, 8 carbon atoms to 12 carbon atoms, 12 carbon atoms to 16 carbon atoms, 16 carbon atoms to 20 carbon atoms, or 20 carbon atoms to 22 carbon atoms.

The foaming agent may further include compositions with Structure 3 for example.

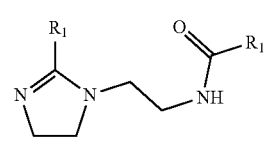

Structure 3

In Structure 3, R1 may be selected from an alkyl group, an alkenyl group, a heteroatom substituted alkyl group, or a heteroatom substituted alkenyl group. Suitable heteroatoms that may be substituted may include, but are not limited to, nitrogen, oxygen, and sulfur, among others. The alkyl or alkenyl (or heteroatom substituted) group R1 may include 5 carbon atoms to 22 carbon atoms. Alternatively, R1 may include 5 carbon atoms to 6 carbon atoms, 6 carbon atoms to 8 carbon atoms, 8 carbon atoms to 12 carbon atoms, 12 carbon atoms to 16 carbon atoms, 16 carbon atoms to 20 carbon atoms, or 20 carbon atoms to 22 carbon atoms.

The foaming agent may further include compositions with Structure 4 for example.

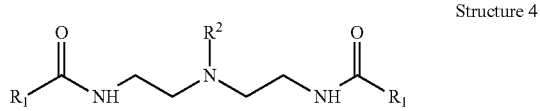

Structure 4

In Structure 4, R1 and R2 may be individually selected from an alkyl group, an alkenyl group, a heteroatom substituted alkyl group, or a heteroatom substituted alkenyl group. Suitable heteroatoms that may be substituted may include, but are not limited to, nitrogen, oxygen, and sulfur, among others. The alkyl or alkenyl (or heteroatom substituted) groups of R1 and R2 may be the same or different, and in some example, R1 may individually include 5 carbon atoms to 22 carbon atoms and R2 may include 1 carbon atom to 8 carbon atoms. Alternatively, R1 may include 5 carbon atoms to 6 carbon atoms, 6 carbon atoms to 8 carbon atoms, 8 carbon atoms to 12 carbon atoms, 12 carbon atoms to 16 carbon atoms, 16 carbon atoms to 20 carbon atoms, or 20 carbon atoms to 22 carbon atoms. Alternatively, R2 may include 1 carbon atom to 3 carbon atoms, 3 carbon atoms to 6 carbon atoms, or 6 carbon atoms to 8 carbon atoms.

Any of Structures 1-4 and any embodiments thereof previously described, collectively referred to as Structures 1-4 herein, may be introduced into a wellbore alone or any combination. Additionally, when present in a treatment fluid comprising a carrier fluid, any of Structures 1-4 may be included in the treatment fluid. When present in a combination, whether introduced alone as a foaming agent or as a foaming agent in a treatment fluid, any of Structures 1-4, may be present in any molar ratio or mass fraction. For example, any of Structures 1-4 may be present in a molar ratio at a point ranging from about 1:1 to about 1:10. Alternatively, any of Structures 1-4 may be present in a molar ratio at a point ranging from about 1:1 to about 1:2, about 1:2 to about 1:4, about 1:4 to about 1:6, about 1:6 to about 1:8, or about 1:8 to about 1:10.

As illustrated, Structures 1-4 may be considered nonionic surfactants due to the neutral charge of the structures. In an example, the foaming agent Structures 1-4 may be protonated to yield a cationic surfactant or protonated foaming agent. Protonation may be accomplished by reaction with an acid to produce the cationic surfactant for different downhole conditions. Suitable acids for protonating Structures 1-4 may include, but are not limited to, mineral acids such as hydrogen halides, halogen oxoacids, sulfuric acid, nitric acid, fluoroboric acid, sulfonic acids, and organic acids such as carboxylic acids, for example. Some additional acids may include, without limitation acetic acid, dodecylbenzenesulfonic acid (DDBSA), acrylic acid, sulfonic acid, alkylsulfonic acid, phosphonic acid and the combination thereof. The acid may be brought in contact with the foaming agent at any time, such as at a surface before the introduction of the foaming agent into a wellbore, during synthesis of the foaming agent, within the wellbore such as in an acid spotting operation, for example. The foaming agent of Structures 1-4 may be fully or partially protonated.

A treatment fluid may include any of the previously described foaming agents and a carrier fluid. The carrier fluid may be any fluid that is operable to transport the foaming agent therein. A carrier fluid may comprise, without limitation, water, liquid hydrocarbon, alcohol, and combinations thereof. The water may comprise brine, seawater, freshwater, water with dissolved solids, or any combinations thereof. The alcohols may comprise $C_3$-$C_{20}$ branched and linear alcohols, for example. The liquid hydrocarbon may be any suitable hydrocarbon, for example, without limitation, $C_5$-$C_{30}$ branched and linear alkanes, alkenes, alkynes, aromatics, diesel, light cycle oils, kerosene, naphtha, crude oil and combinations thereof.

The foaming agent and carrier fluid may be present in the treatment fluid in any ratio or mass fraction suitable for a particular application. In an example, the foaming agent may be present in the treatment fluid in an amount of about 20% to about 60% by weight of the treatment fluid. Alternatively foaming agent may be present in an amount of about 20% to about 30% by weight of the treatment fluid, about 30% to about 40% by weight of the treatment fluid, about 40% to about 50% by weight of the treatment fluid, or about 50% to about 60% by weight of the treatment fluid. One of ordinary skill in the art will recognize an appropriate amount of dual action foaming agent and corrosion inhibitor for a particular application.

A method us using any of the previously described foaming agents or treatment fluids including the foaming agents may include placement into a wellbore penetrating a subterranean formation. The wellbore may include a perforated conduit extending from a producing zone in the subterranean formation to a surface where formation fluids may exit the wellbore. The wellbore may include fluids such as gas, oil, condensate, water, or any combinations thereof contained within the wellbore. The fluids may be produced from the subterranean formation or be previously introduced into the wellbore during a downhole operation, for example. The fluids in the wellbore may exert pressure of the subterranean formation thereby decreasing a differential pressure between a surface of the wellbore, such as a wellhead, and the subterranean formation. In an example, fluids present in the wellbore may form a full or partial column within the wellbore.

The foaming agents or treatment fluids including the foaming agents may be introduced into the wellbore by any method including introducing the foaming agent or treatment fluid containing the foaming agent into a tubular disposed in the wellbore, introducing through an annulus formed between one or more tubulars disposed in the wellbore, or introducing through a production line (or production tubing), for example. In examples, the foaming agents or treatment fluids containing the foaming agents may be continuously or intermittently introduced into the wellbore as desired. As previously discussed, foaming of a formation fluid may be beneficial to, for example, reduce hydrostatic pressure in the wellbore to increase the differential pressure between the producing zone of a subterranean formation and a surface where the formation fluids are produced. The foaming agent or treatment fluid containing the foaming agent may interact with fluids present in the wellbore and cause fluids present in the wellbore to foam. The foaming action, in some examples, may be spontaneous without further input required to cause at least a portion of fluids present in the wellbore to form a foam. The foam quality, or volume percent gas within a foam at a specified temperature and pressure may be selected for a particular application. The foam quality of the fluids in the wellbore may be a foam quality at a point in a range of about 10% quality to about 99% quality. Alternatively, the foam quality may be at a point in a range of about 10% quality to about 30% quality, about 30% quality to about 60% quality, or about 60% quality to about 99% quality. Foam quality may be affected my factors such as, without limitation, a flow rate of the foaming agents or treatment fluids including the foaming agents into the wellbore, chemical identity of the foaming agents, chemical identity of the fluids present in the wellbore, pressure, temperature, and presence of a foaming gas, for example. In an alternate example, the foaming agents or treatment fluids containing the foaming agents may be used to deliquefy a transmission line. A transmission line may include production tubing, production casing, a flow line, or a pipeline for example.

The foaming agents or treatment fluids containing the foaming agents may be introduced into the wellbore alone or in combination with a foaming gas, example. The foaming gas may be any suitable gas for foaming the formation fluids and treatment fluid. For example, without limitation, the foaming gas may comprise air, nitrogen, $CO_2$, natural gas, and combinations thereof. The foaming gas may be introduced at any rate, pressure, and temperature as desired to cause any quality of foam to form in the wellbore.

Any suitable technique may be used for introduction of the foaming agents or treatment fluids including the foaming agents into the wellbore. The foaming agents or treatment fluids including the foaming agents may be introduced into the wellbore with a secondary lift system in any suitable manner as will be described in detail below. The foaming agents or treatment fluids including the foaming agents may be introduced into the wellbore at any suitable location or at multiple locations within the wellbore. For example, the foaming agents or treatment fluids including the foaming agents may be introduced below a producing zone or perforations, between perforations, above perforations, below a column of wellbore fluid, into a column of wellbore fluid, above a column of wellbore fluid, or any other place within the wellbore.

In an example, the foaming agents or treatment fluids including the foaming agents may be introduced into the wellbore by way of annulus drip, a slip stream, a capillary string, or batch treatments. The annulus drip technique may include introduction of the foaming agents or treatment fluids including the foaming agents into the wellbore at the wellhead in the annulus between the production tubing and production casing. The foaming agents or treatment fluids including the foaming agents may then fall (or drip) to the bottom of the wellbore whereby contact may be made with wellbore fluids and cause the wellbore fluids to foam to a foamed mixture. The foamed mixture may be produced back up through the production tubing where the foaming agent may contact downhole equipment and provide anti-corrosion protection for surfaces. The slip stream technique may include application of the treatment fluid into a slip stream of produced wellbore fluids that may be introduced into the annulus between the production tubing and production casing. The foaming agents or treatment fluids including the foaming agents may then fall (or drip) to the bottom of the wellbore and be produced back up through the production tubing where it may contact downhole equipment. A valve may be used in the regulation the volume of the treatment fluid delivered into the slip stream. The capillary stream technique may include introduction of the treatment fluid into the wellbore through a capillary tube that extends down the annulus to the bottom of the wellbore. The capillary tube may be a small diameter tube, for example, about ¼ inches (0.6 cm) to about ⅜ inches (0.95 cm) in outer diameter. The batch technique may include pumping a large volume of the foaming agents or treatment fluids including the foaming agents into the annulus. A pump truck or other suitable pump may be used to displace the treatment fluid to the bottom of the wellbore. By introducing a large volume, residual concentrations of foaming agents or treatment fluids including the foaming agents may continue to provide wear resistance and foaming even after treatment. In an example, the treatment fluid may be mixed before injection. In an example, the treatment fluid may be mixed downhole after injection.

In certain examples, the foaming agents or treatment fluids including the foaming agents may be continuously introduced into the wellbore. Continuous application may be used in any suitable treatment technique, including, but not limited to, annulus drip, slip stream, or capillary string, among others. In contrast to batch treatments, continuous introduction may include continuation application of the foaming agents or treatment fluids including the foaming agents, for example, by way of the treatment fluid into the wellbore, for extended period of time, for example, for about 1 day, about 1 week, about 1 month, about 6 months, about 1 year, or even longer.

The foaming agents or treatment fluids containing the foaming agents may be introduced into any wellbore at any stage of production. The treatment fluid may be used in primary recovery applications such as naturally flowing wells, secondary recovery applications such as artificial lift applications, and in tertiary recovery application such as enhanced oil recovery operations. As previously mentioned, the disclosed foaming agents may have anti-corrosion properties which may be beneficial in the treatment of wellbores with surfaces that may be corroded. The foaming agents or treatment fluids containing the foaming agents may be introduced into the wellbore and contact downhole equipment to provide protection against material corrosion and wear (erosion) and to increase differential pressure in the wellbore.

In some examples, the foaming agents or treatment fluids containing the foaming agents may be introduced into a wellbore containing a secondary lift system. In examples including a secondary lift system, the foaming agents or treatment fluids containing the foaming agents may be introduced by any of the previously described methods including, for example, through a production line disposed within the wellbore. A secondary lift system may be any suitable system capable of lowering the producing bottom hole pressure on the formation to obtain a higher production rate from the well. Suitable secondary lift systems may include, but are not limited to, sucker rod lift system, plunger lift system, and the like. One type of secondary lift system may include a sucker rod lift system. A sucker rod lift system may include a prime mover, a beam pump, a sucker rod string, a positive displacement pump, and valves. The prime mover may provide sufficient energy to turn a crank arm. The crank arm may be connected to a beam which may cause the beam to reciprocate. The resulting reciprocating movement up and down may lift and lower a rod string that may be attached to one end of the beam. The reciprocating motion of the rod string may open, and close valves located in the positive displacement pump downhole. Any suitable valves may be used. Any suitable positive displacement pump may be used. Depending on the position of the valves, a fluid may be captured or allowed to flow into the wellbore. The foaming agents or treatment fluids containing the foaming agents may mix with fluids present in the wellbore and cause the production of a foam with lower density than the fluid in the wellbore. The foaming agents or treatment fluids containing the foaming agents and fluids present in the wellbore may form a foamed mixture of any quality as described above. The mixture may then enter the positive displacement pump, wherein the foaming agents or treatment fluids containing the foaming agents and the wellbore fluids may flow through the positive displacement pump and into the production tubing, also referred to herein as tubing. The foaming agents or treatment fluids containing the foaming agents may continuously contact the production tubing, the sucker rod string, and the outside of the positive displacement pump, as it leaves the wellbore. This contact may provide erosion-corrosion resistance and/or reduce the wear exhibited on the production tubing, the sucker rod string, and the outside of the positive displacement pump. It should be understood that the above description of the sucker rod lift system is merely exemplary and suitable sucker rod lift system may be otherwise arranged as may be applicable for particular application.

Another type of secondary lift system may include a plunger lift system. Any plunger lift system capable of removing liquids from the wellbore so that the well may be produced at low bottom hole pressures. In an example, the plunger lift system may include downhole and surface equipment. The downhole equipment may include a plunger, a bottom hole bumper spring, and a standing valve. The plunger may include a bypass valve. Optionally, the plunger may be a piston which may include a bypass valve. The plunger or the piston may travel through the production tubing further into the wellbore where it may land on a bottom hole bumper spring. Any suitable plunger capable of moving within the tubing unhindered while creating a mechanical seal between the fluids above and below the plunger when the bypass valve is closed may be used. A tubing anchor may be fixed to the end of the tubing disposed downhole. Any tubing anchor capable of minimizing the movement of the tubing may be used. At the surface, a motor valve assembly may automatically regulate production via a controller. Any suitable controller may be used. A short section of pipe that may extend above the wellhead may serve to catch the plunger after the plunger or piston reaches the surface. The foaming agents or treatment fluids containing the foaming agents may be introduced at the wellhead by any of the previously described methods, for example. In an example the foaming agents or treatment fluids containing the foaming agents may be placed down hole via an annulus between the wellbore casing and the production tubing. The foaming agents or treatment fluids containing the foaming agents may mix with the fluids present in the wellbore and cause the fluid to form a foamed mixture. As the plunger travels through the production tubing, the foamed mixture of treatment fluid and wellbore fluids may be displaced thereby contacting the production tubing, the plunger, the bottom hole bumper spring, and the tubing stop. The foaming agents or treatment fluids containing the foaming agents may provide corrosion and material-on-material erosion resistance to said downhole equipment as well as foam the wellbore fluids. It should be understood that the above description of the plunger lift system is merely exemplary and suitable plunger lift system may be otherwise arranged as may be applicable for particular application.

Example methods of using the foaming agents or treatment fluids including the foaming agents for foaming wellbore fluids will now be described in more detail with reference to FIG. 1. Any of the previous examples or embodiment of foaming agents or treatment fluids including the foaming agents may apply in the context of FIG. 1.

FIG. 1 illustrates secondary lift system 100. Secondary lift system 100 may include any suitable secondary lift system 100 capable of lowering the producing bottom hole pressure on subterranean formation 114 to obtain a higher production rate from wellbore 118. As illustrated, secondary lift system 100 may be a rod pump system. Although only one type of list system is illustrated, it will be apparent to those of ordinary skill in the art how to apply the disclosure herein to other types of lift systems. Secondary lift system may include equipment at surface 102 and disposed within subterranean formation 114. Equipment at surface 102 may include, but is not limited to, prime mover 106, pumping unit 110, wellhead 112, and rod string 120. Prime mover 106 may be any unit capable of providing sufficient energy to pumping unit 110. In an example, prime mover 106 may be an internal combustion engine, an electrical motor, or the like. Pumping unit 110 may be any pumping unit capable of converting rotational motion created by prime mover 106 into a reciprocating vertical motion. The reciprocating vertical motion may lift and lower rod string 120 within wellbore 132. Rod string 120 may include a plurality of sucker rods 122 connected in sequence and disposed within production tubing 124. Sucker rods 122 may be of any suitable length, diameter, and material. Disposed below the plurality of sucker rods 122, near the producing zone and perforations 116, may be downhole pump 140. Perforations 116 may allow the produced fluid to flow into and out of the subterranean formation 114. Downhole pump 140 may be actuated by reciprocating vertical motion of rod string 120.

Treatment fluid 150 may be introduced into wellbore 118. Treatment fluid 150 may be any treatment fluid as previously described including foaming agents or treatment fluids including the foaming agents. For example, treatment fluid 150 may comprise a foaming agent and a carrier fluid. As illustrated, treatment fluid 150 may introduced into annulus 134 between production tubing 124 and casing 136. However, one of ordinary skill in the art will appreciate that treatment fluid 150 may be introduced into wellbore 118 by any other means, such as, without limitation, a production line (not illustrated). Treatment fluid 150 may be introduced into wellbore 132 in any suitable manner. In an example, treatment fluid 150 may be injected into wellbore 118 at wellhead 112. In an example, treatment fluid 150 may be continuously provided to wellbore 118. Suitable techniques for introduction of treatment fluid 150 may include, but are not limited to, annulus drip, slip stream, capillary string, or batch treatments. As illustrated, treatment fluid 150 may be introduced to wellbore at wellhead 112 by way of annulus drip. Treatment fluid may flow through wellhead 112 and into annulus 134 formed between production tubing 124 and casing 136. Treatment fluid 150 may fall and/or drip to the bottom of wellbore 118. At the bottom of wellbore 132, treatment fluid 150 may mix with the produced fluids 138. The mixture 142 of treatment fluid 150 and produced fluids 138 may then be pumped through downhole pump 140 and up production tubing 124. As the mixture 142 of treatment fluid 150 and the produced fluids 138 flow through secondary lift system 100, the lubricating agent and corrosion inhibitor in the treatment fluid 150 and the produced fluids may continuously be in contact with production tubing 124, sucker rods 122, and downhole pump 140, in turn which may provide production tubing 124, sucker rods 122, and downhole pump 140 with corrosion and metal-on-metal erosion resistance. This provided resistance may reduce the wear on said components of secondary lift system 100 and in turn extend their production life.

Figure 2:
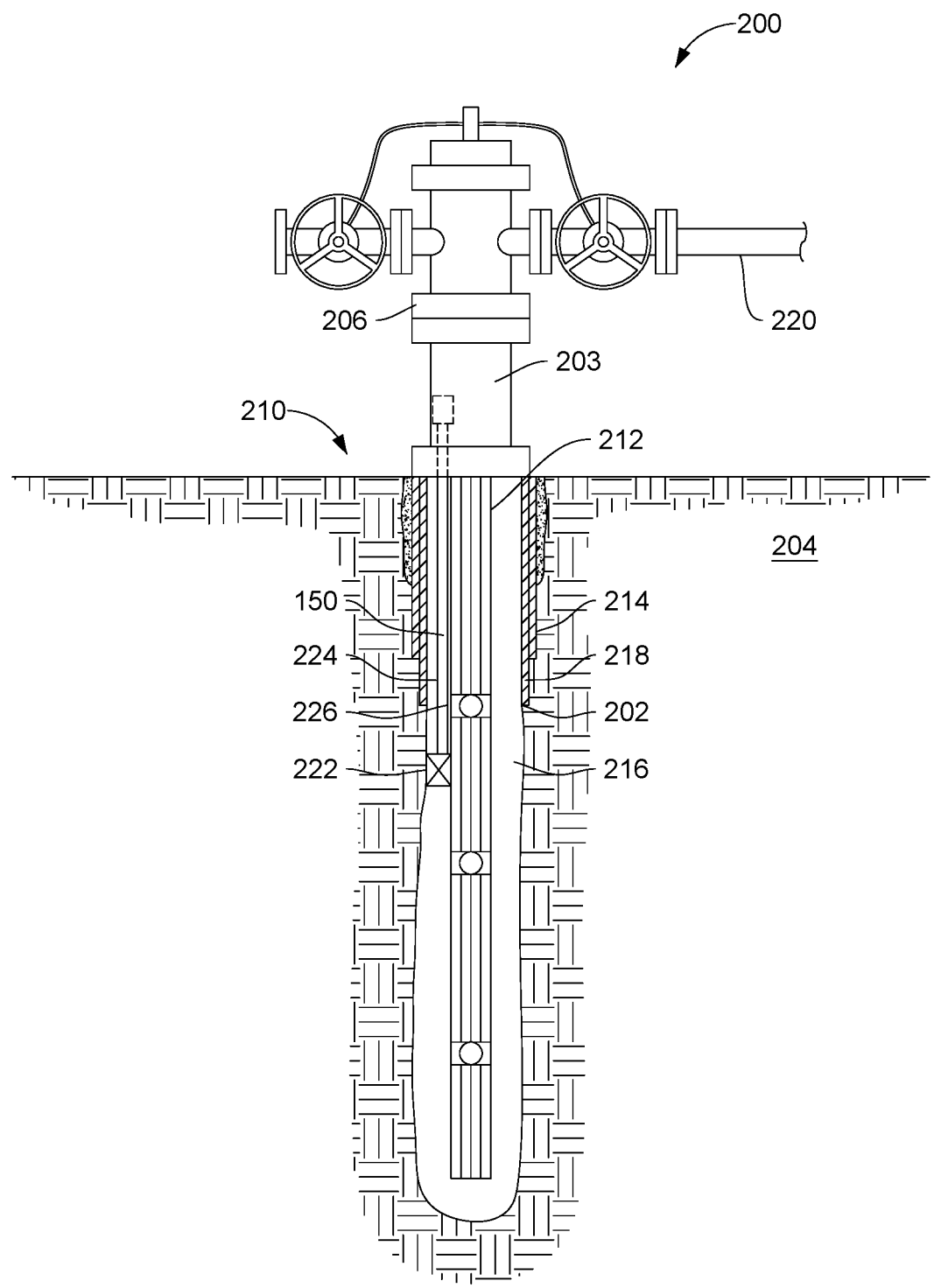
FIG. 2 is a schematic illustration of an example producing well.

FIG. 2 illustrates a production fluid recovery system 200 disposed in a wellbore 202. Production fluid recovery system 200 may comprise a wellbore 202 formed within a formation 204. Wellbore 202 may be a vertical wellbore as illustrated or it may be a horizontal and/or a directional well. While production fluid recovery system 200 may be illustrated as land-based, it should be understood that the present techniques may also be applicable in offshore applications. Formation 204 may be made up of several geological layers and include one or more hydrocarbon reservoirs. As illustrated, production fluid recovery system 200 may include a production tree 206 and a wellhead 208 located at a well site 210. A production tubing 212 or a plurality of production tubing 212 may be coupled to production tree 206 and extend from wellhead 208 into wellbore 202, which may traverse formation 204.

In examples, wellbore 202 may be cased with one or more casing segments 214. Casing segments 214 help maintain the structure of wellbore 202 and prevent wellbore 202 from collapsing in on itself. In some examples, a portion of the well may not be cased and may be referred to as "open hole." The space between production tubing 212 and casing segments 214 or wellbore wall 216 may be an annulus 218. Production fluid may enter annulus 218 from formation 204 and then may enter production tubing 212 from annulus 218. Production tubing 212 may carry production fluid uphole to production tree 206. Production fluid may then be delivered to various surface facilities for processing via a surface pipeline 220.

In examples, wellbore 202 may be separated into a plurality of zones and may comprise any number of various tools that may help in the recovery of production fluids from formation 204. As disclosed, production fluid recovery system 200 may comprise chemical injection system 222. Chemical line 226 may provide treatment fluid 150 to be disposed in annulus 218, wellbore 202, and/or production tubing 212. Fluids may flow at any desired rate from the surface through chemical injection system 222 to annulus 218, wellbore 202, and/or production tubing 212. In examples, chemical injection system 222 may connect to wellhead 208 through a pilot line 224 and a chemical line 226.

The exemplary treatment fluid disclosed herein may directly or indirectly affect one or more components or pieces of equipment associated with the preparation, delivery, recapture, recycling, reuse, and/or disposal of the treatment fluid. For example, the treatment fluid particulates may directly or indirectly affect one or more mixers, related mixing equipment, mud pits, storage facilities or units, composition separators, heat exchangers, sensors, gauges, pumps, compressors, and the like used to generate, store, monitor, regulate, and/or recondition the treatment fluid. The treatment fluid may also directly or indirectly affect any transport or delivery equipment used to convey the treatment fluid to a well site or downhole such as, for example, any transport vessels, conduits, pipelines, trucks, tubulars, and/or pipes used to compositionally move the treatment fluid from one location to another, any pumps, compressors, or motors (e.g., topside or downhole) used to drive the treatment fluid into motion, any valves or related joints used to regulate the pressure or flow rate of the treatment fluid particulates (or fluids containing the same treatment fluid particulates), and any sensors (i.e., pressure and temperature), gauges, and/or combinations thereof, and the like. The disclosed treatment fluids may also directly or indirectly affect the various downhole equipment and tools that may come into contact with the treatment fluid such as, but not limited to, wellbore casing, wellbore liner, completion string, insert strings, drill string, coiled tubing, slickline, wireline, drill pipe, drill collars, mud motors, downhole motors and/or pumps, cement pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like.

Accordingly, the present disclosure may provide methods, systems, and apparatus that may relate to recovering oils and/or water from hydrocarbon contaminated solids and generate a pipeline oil feed. The methods, systems, and apparatus may include any of the various features disclosed herein, including one or more of the following statements.

Statement 1. A method including: placing into a wellbore penetrating a subterranean formation a foaming agent, wherein the wellbore comprises a produced fluid from the subterranean formation; and foaming the produced fluid.

Statement 2. The method of statement 1 wherein the foaming agent comprises the following structure:

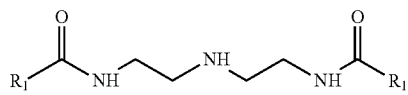

wherein R1 is selected from an alkyl group, an alkenyl group, a heteroatom substituted alkyl group, or a heteroatom substituted alkenyl group and wherein R1 comprises 1 carbon atom to 22 carbon atoms.

Statement 3. The method of statement 2 wherein R1 is the alkyl group and wherein R1 comprises 8 carbon atoms to 12 carbon atoms.

Statement 4. The method of statement 1 wherein the foaming agent comprises the following structure:

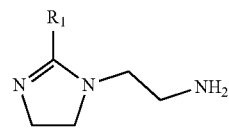

wherein R1 is selected from an alkyl group, an alkenyl group, a heteroatom substituted alkyl group, or a heteroatom substituted alkenyl group and wherein R1 comprises 1 carbon atom to 22 carbon atoms.

Statement 5. The method of statement 4 wherein R1 is the alkyl group and wherein R1 comprises 8 carbon atoms to 12 carbon atoms.

Statement 6. The method of statement 1 wherein the foaming agent comprises the following structure:

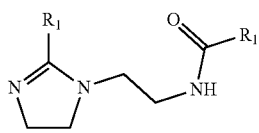

wherein R1 is selected from an alkyl group, an alkenyl group, a heteroatom substituted alkyl group, or a heteroatom substituted alkenyl group and wherein R1 comprises 5 carbon atoms to 22 carbon atoms.

Statement 7. The method of statement 6 wherein R1 is the alkyl group and wherein R1 comprises 8 carbon atoms to 12 carbon atoms.

Statement 8. The method of statement 1 wherein the foaming agent comprises the following structure:

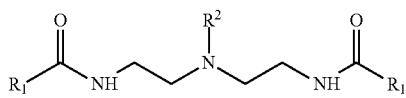

wherein R1 and R2 are individually selected from an alkyl group, an alkenyl group, a heteroatom substituted alkyl group, or a heteroatom substituted alkenyl group, wherein R1 comprises 5 carbon atoms to 22 carbon atoms in length, and wherein R2 comprises 1 carbon atom to 8 carbon atoms.

Statement 9. The method of any of statements 1-8 wherein foaming agent is present in a treatment fluid, the treatment fluid comprising the foaming agent and a carrier fluid.

Statement 10. The method of any of statements 1-9 wherein the carrier fluid is selected from the group consisting of water, a liquid hydrocarbon, an alcohol, and combinations thereof.

Statement 11. The method of any of statements 1-10 further comprising placing a foaming gas in the wellbore.

Statement 12. The method of any of statements 1-11 wherein the foaming agent is placed in the wellbore through a production line disposed within the wellbore.

Statement 13. A method comprising: introducing a foaming agent into a wellbore; and foaming a fluid present in the wellbore, wherein the foaming agent is at least one of the following structures:

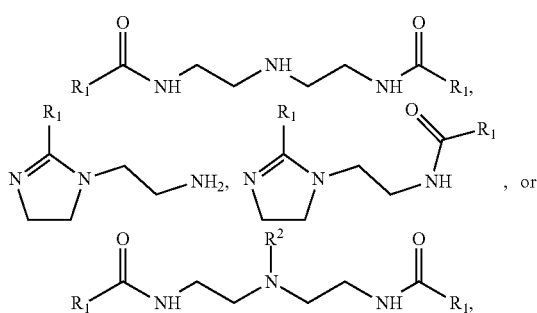

wherein R1 and R2 are individually selected from an alkyl group, an alkenyl group, a heteroatom substituted alkyl group, or a heteroatom substituted alkenyl group, wherein R1 comprises 5 carbon atoms to 22 carbon atoms in length, and wherein R2 comprises 1 carbon atom to 8 carbon atoms.

Statement 14. The method of statement 13 wherein foaming agent is introduced into the wellbore via an annulus drip, a slip stream, a capillary string, production line, or a combination thereof.

Statement 15. The method of any of statements 12-14 wherein the foaming agent has a corrosion inhibition property and slows corrosion on at least one surface of equipment disposed within the wellbore.

Statement 16. The method of any of statements 12-15 wherein the foaming agent is introduced into the wellbore during an artificial lift operation.

Statement 17. The method of any of statements 12-16 wherein the foaming agent is protonated by an acid before or during the step of introducing to form a protonated foaming agent.

Statement 18. A method comprising: introducing a treatment fluid into a wellbore, the treatment fluid comprises: a foaming agent and a carrier fluid comprising a C3-C10 alcohol, wherein the foaming agent is present in an amount of about 20% to about 60% by weight of the treatment fluid, wherein the foaming agent is:

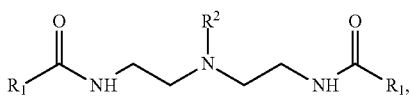

and wherein R1 and R2 are individually selected from an alkyl group, an alkenyl group, a heteroatom substituted alkyl group, or a heteroatom substituted alkenyl group, wherein R1 is 5 carbon atoms to 22 carbon atoms in length, and wherein R2 is 1 carbon atom to 8 carbon atoms; and foaming a fluid in the wellbore.

Statement 19. The method of statement 18 wherein foaming agent is introduced into the wellbore via a production line.

Statement 20. The method of any of statements 18-19 further comprising protonating the foaming agent with an acid before or during the step of introducing to form a protonated foaming agent.

To facilitate a better understanding of the present disclosure, the following examples of certain aspects of some of the systems and methods are given. In no way should the following examples be read to limit, or define, the entire scope of the disclosure.

Example 1

A foam test was conducted using a Teclis Scientific FOAMSCAN® foam analyzer. The foam analyzer instrument utilizes cameras to capture images of foam created over time to measure foam volume, liquid volume, and liquid fraction, among other parameters, for a particular foam sample. The test setup comprised a double walled column jacketed with connections to a recirculating bath for maintaining constant system temperature. The column further comprise a porous glass frit positioned at the base of the column connected to a methane supply.

Figure 3:
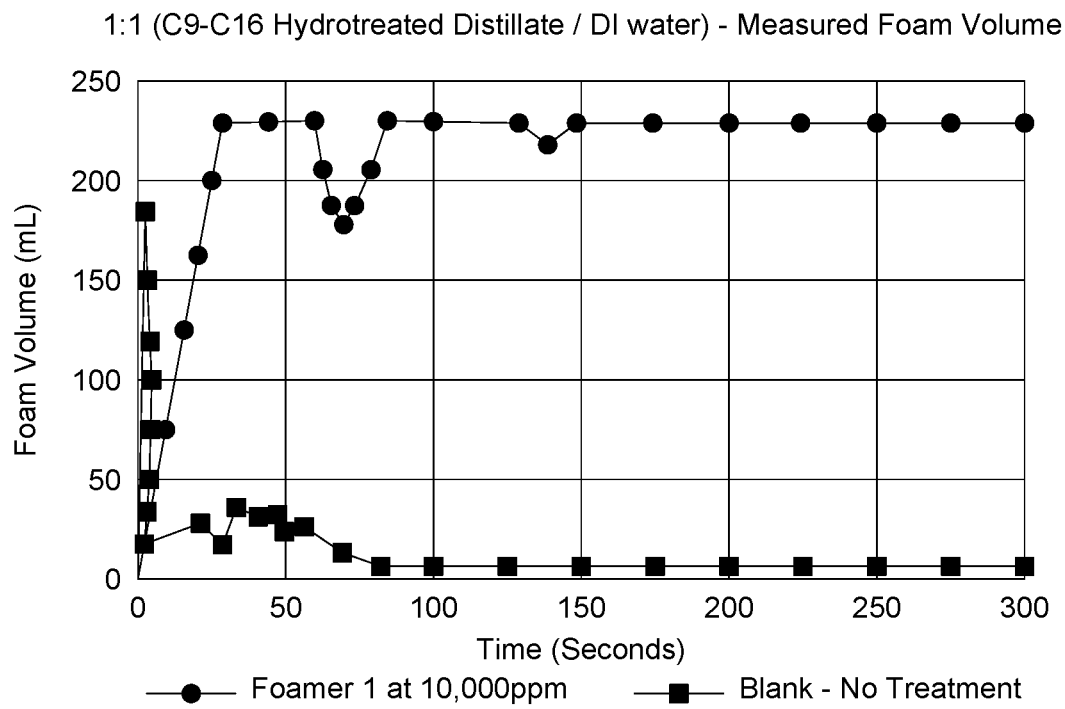
FIG. 3 is graph of a result of a foaming test.
Figure 4:
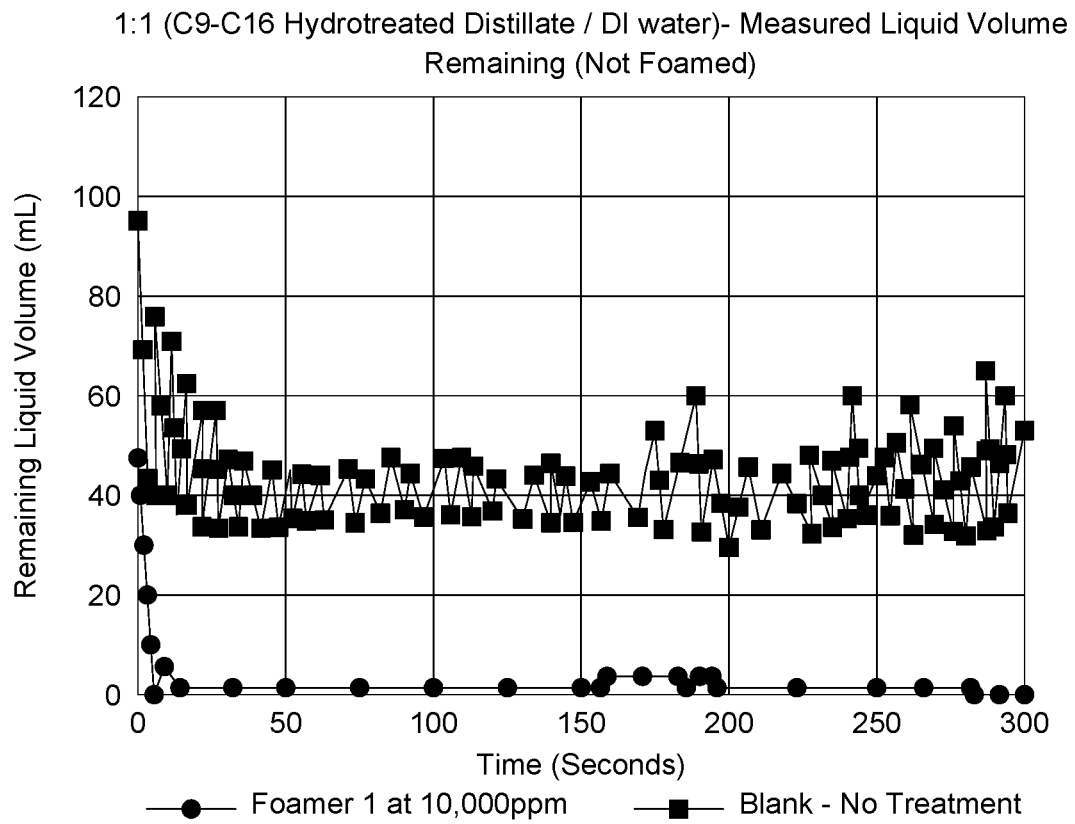
FIG. 4 is graph of a result of a foaming test.

A test was prepared at 60° C. using two 50 mL samples of a 50/50 mixture of $C_9$-$C_{16}$ hydrotreated distillate and deionized water. The first sample was treated with 10,000 ppm of foamer and the second sample was kept as a control. The samples were individually tested in the column as described above. 400 mL/minute of methane gas was passed through each sample for 5 minutes while data was logged. The results are illustrated in FIGS. 2-3.

It was observed that the sample treated with foamer contained about 230 mL of foam after 5 minutes while the control yielded less than 25 mL of foam. It was further observed that the amount of liquid volume carried into the foam column during the test was significantly greater for the treated sample than the control.

Example 2

Figure 5:
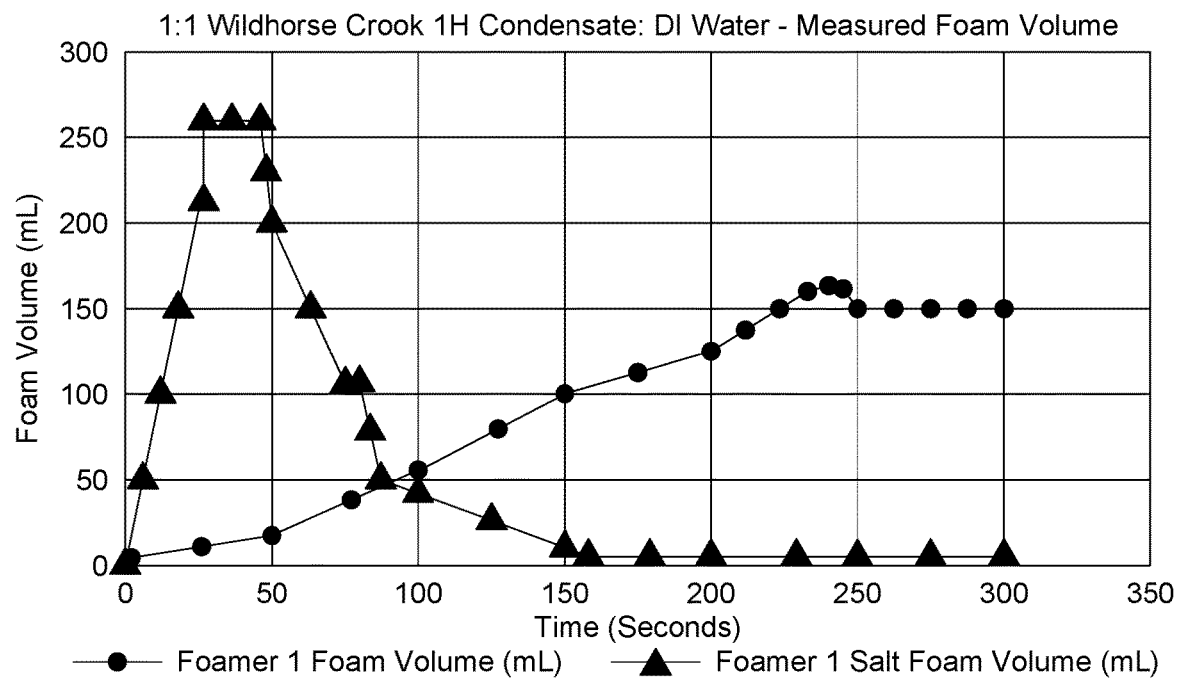
FIG. 5 is graph of a result of a foaming test.

In another experiment, testing was conducted using crude oil Wildhorse Crook 1H which has an API gravity measure of 42.3 and distilled water. Aliquots of the oil and water mixture was individually treated with 10,0000 ppm of a foamer and a cationic salt of the foamer. The cationic salt of the foamer was prepared by salting the foamer with methane sulfonic acid. The aliquots were individually tested in the column as described above. The results of the experiment are shown in FIG. 5. It was observed that the cationic foamer generates foam earlier than the neutral foamer. It was further observed that the neutral foamer generates a stable foam with the tested crude oil whereas the cationic foamer generates a less stable foam.

Example 3

Figure 6:
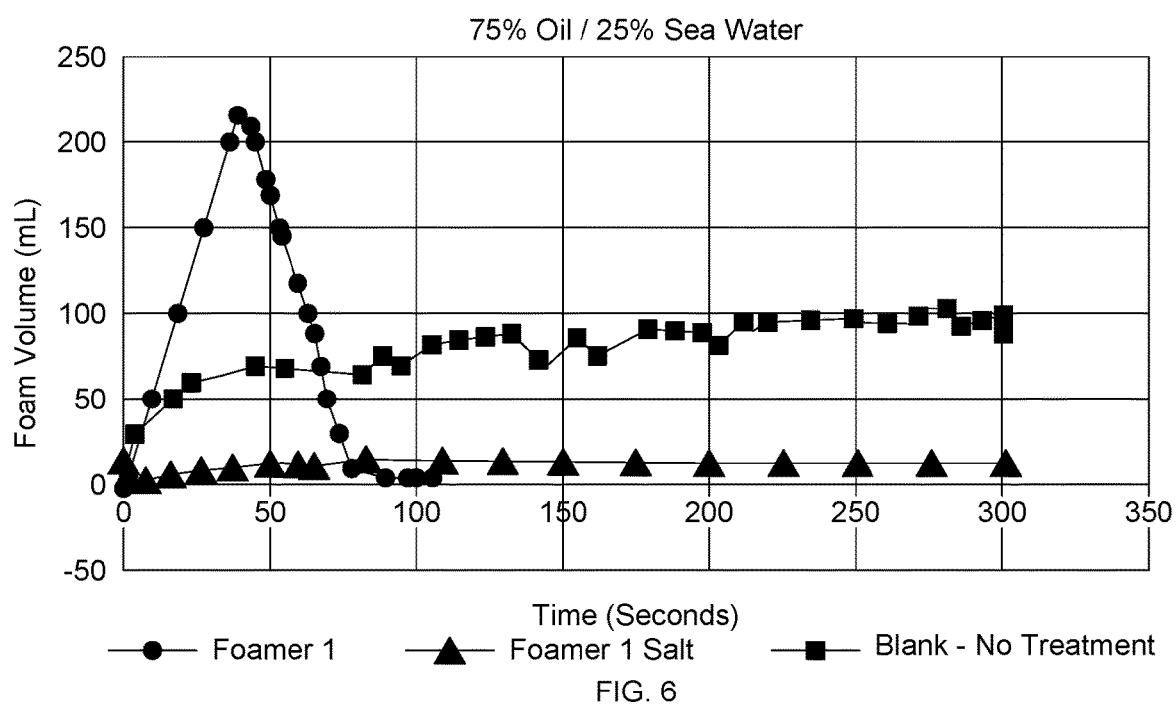
FIG. 6 is graph of a result of a foaming test.
Figure 7:
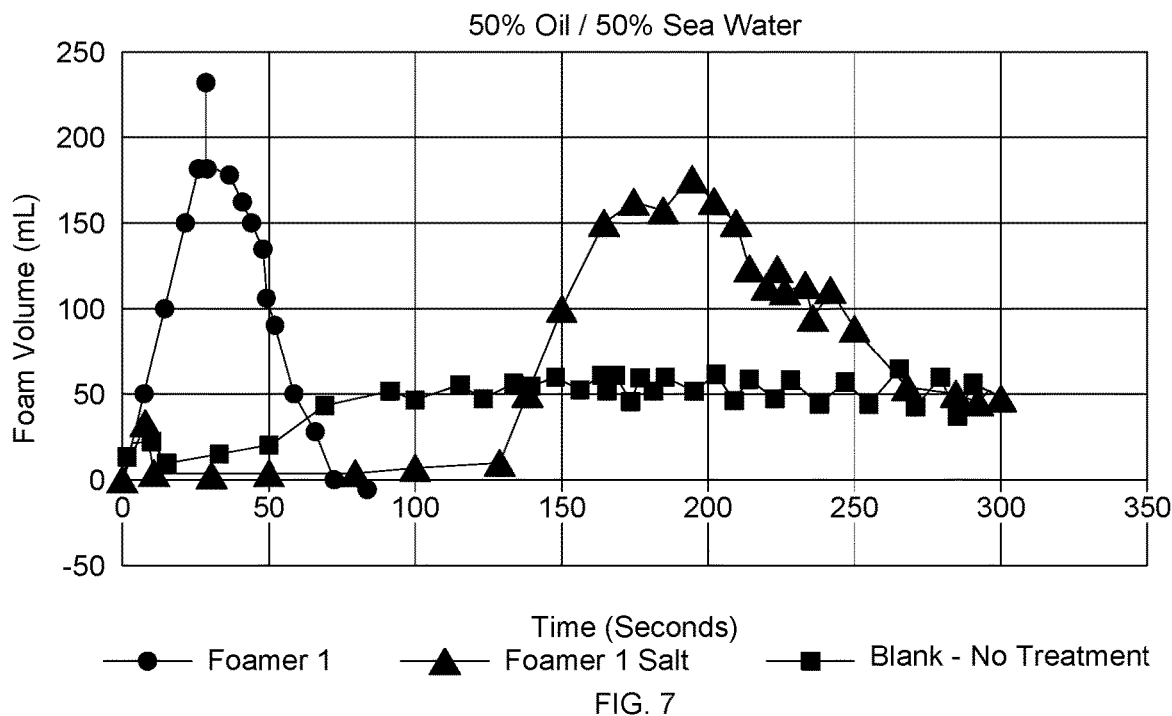
FIG. 7 is graph of a result of a foaming test.
Figure 8:
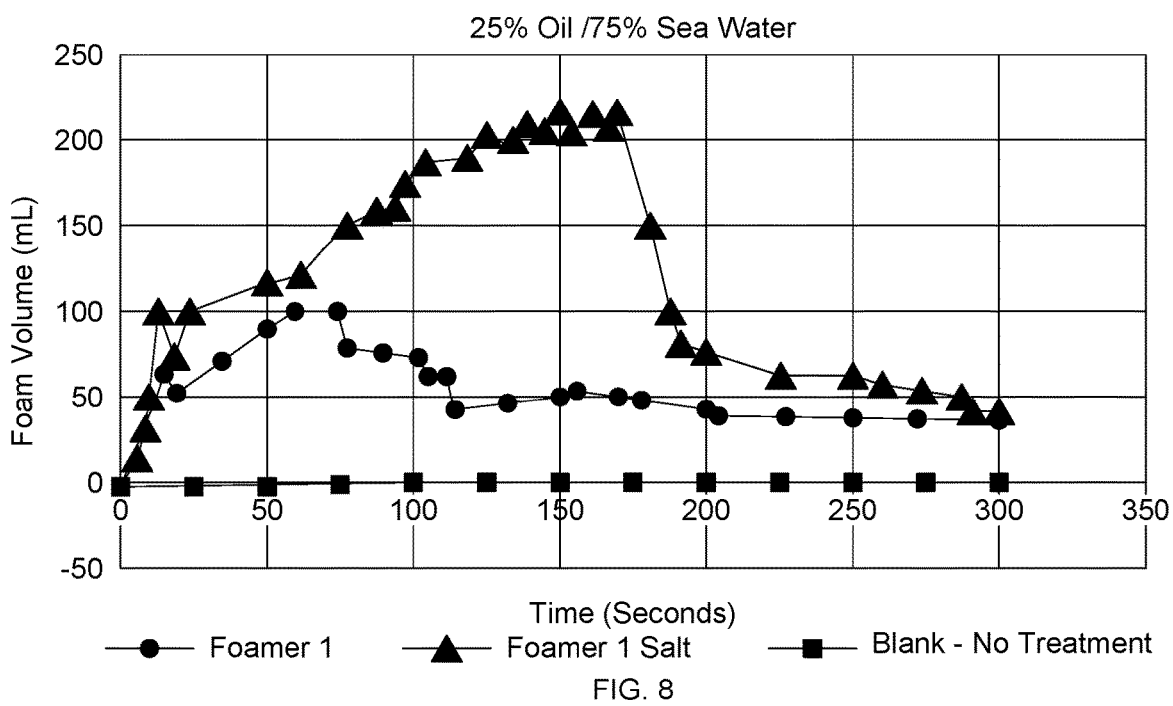
FIG. 8 is graph of a result of a foaming test.

In another experiment, effectiveness of foamers of experiment 3 in 'salted' water was evaluated. A test was conducted using Wildhorse Crook 1H oil and synthetic seawater prepared by dissolving salts in water. Three different ratios of oil to seawater were prepared at 75/25, 50/50, and 25/75 and aliquots of each of the three water to oil ratios were individually treated with 10,0000 ppm of the foamer and the cationic salt of the foamer. The aliquots were individually tested in the column as described above. The results of the experiment are shown in FIGS. 6-8. It was observed that the neutral foamer performed better in higher oil concentration water while the cationic foamer performed better in higher water concentration. The blank aliquot indicates the behavior of each fluid combination under the same test conditions without the addition of the foamer.

The preceding description provides various embodiments of the spacer fluids containing different additives and concentrations thereof, as well as methods of using the spacer fluids. It should be understood that, although individual embodiments may be discussed herein, the present disclosure covers all combinations of the disclosed embodiments, including, without limitation, the different additive combinations, additive concentrations, and fluid properties.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method comprising:
   introducing a foaming agent into a wellbore; and
   foaming a fluid present in the wellbore,
   wherein the foaming agent is at least one of the following structures:

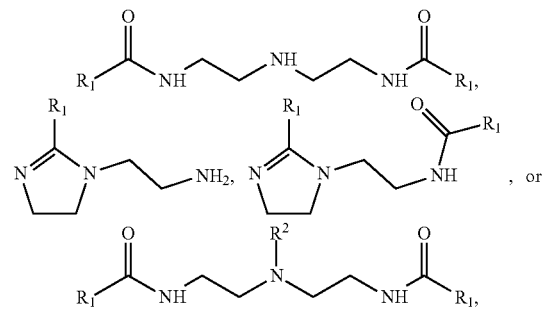

wherein R1 and R2 are individually selected from an alkyl group, an alkenyl group, a heteroatom substituted alkyl group, or a heteroatom substituted alkenyl group, wherein R1 comprises 5 carbon atoms to 22 carbon atoms in length, and wherein R2 comprises 1 carbon atom to 8 carbon atoms.

2. The method of claim 1 wherein foaming agent is introduced into the wellbore via an annulus drip, a slip stream, a capillary string, production line, or a combination thereof.

3. The method of claim 1 wherein the foaming agent has a corrosion inhibition property and slows corrosion on at least one surface of equipment disposed within the wellbore.

4. The method of claim 1 wherein the foaming agent is introduced into the wellbore during an artificial lift operation.

5. The method of claim 1 wherein the foaming agent is protonated by an acid before or during the step of introducing to form a protonated foaming agent.

6. A method comprising:
   placing into a wellbore penetrating a subterranean formation a foaming agent, wherein the wellbore comprises a produced fluid from the subterranean formation, and wherein the foaming agent comprises the following structure:

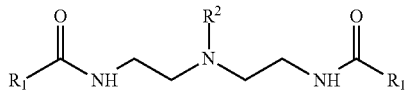

wherein R1 and R2 are individually selected from an alkyl group, an alkenyl group, a heteroatom substituted alkyl group, or a heteroatom substituted alkenyl group, wherein R1 comprises 5 carbon atoms to 22 carbon atoms in length, and wherein R2 comprises 1 carbon atom to 8 carbon atoms; and foaming the produced fluid.

7. The method of claim 6 wherein foaming agent is present in a treatment fluid, the treatment fluid comprising the foaming agent and a carrier fluid.

8. The method of claim 7 wherein the carrier fluid is selected from the group consisting of water, a liquid hydrocarbon, an alcohol, and combinations thereof.

9. The method of claim 6 further comprising placing a foaming gas in the wellbore.

10. The method of claim 6 wherein the foaming agent is placed in the wellbore through a production line disposed within the wellbore.

11. A method comprising:

introducing a treatment fluid into a wellbore, the treatment fluid comprises: a foaming agent and a carrier fluid comprising a C3-C10 alcohol, wherein the foaming agent is present in an amount of about 20% to about 60% by weight of the treatment fluid, wherein the foaming agent is:

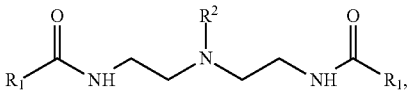

and wherein R1 and R2 are individually selected from an alkyl group, an alkenyl group, a heteroatom substituted alkyl group, or a heteroatom substituted alkenyl group, wherein R1 is 5 carbon atoms to 22 carbon atoms in length, and wherein R2 is 1 carbon atom to 8 carbon atoms; and foaming a fluid in the wellbore.

12. The method of claim 11 wherein foaming agent is introduced into the wellbore via a production line.

13. The method of claim 11 further comprising protonating the foaming agent with an acid before or during the step of introducing to form a protonated foaming agent.

* * * * *